(12) United States Patent
Vesselov et al.

(10) Patent No.: US 12,311,190 B2
(45) Date of Patent: May 27, 2025

(54) APPARATUS AND METHOD FOR IRRADIATING INSIDE AN OBJECT

(71) Applicant: Theralase Technologies Inc., Toronto (CA)

(72) Inventors: Leonid Vesselov, Milton (CA); Roger J. Dumoulin-White, Toronto (CA)

(73) Assignee: Theralase Technologies Inc., Toronto (CA)

( * ) Notice: Subject to any disclaimer, the term of this patent is extended or adjusted under 35 U.S.C. 154(b) by 0 days.

(21) Appl. No.: 17/008,497

(22) Filed: Aug. 31, 2020

(65) Prior Publication Data

US 2022/0062654 A1    Mar. 3, 2022

(51) Int. Cl.
*A61N 5/06* (2006.01)
*A61N 5/067* (2006.01)

(52) U.S. Cl.
CPC .......... *A61N 5/0603* (2013.01); *A61N 5/062* (2013.01); *A61N 2005/061* (2013.01); *A61N 2005/063* (2013.01); *A61N 2005/0666* (2013.01); *A61N 5/067* (2021.08)

(58) Field of Classification Search
CPC ...... A61N 5/0603; A61N 5/062; A61N 5/067; A61N 2005/061; A61N 2005/063; A61N 2005/0666
See application file for complete search history.

(56) References Cited

U.S. PATENT DOCUMENTS

| | | | |
|---|---|---|---|
| 5,125,925 A | 6/1992 | Lundahl | |
| 5,292,320 A | 3/1994 | Brown et al. | |
| 6,413,267 B1 | 7/2002 | Dumoulin-White et al. | |
| 6,962,910 B2 | 11/2005 | Brewer et al. | |
| 7,612,057 B2 | 11/2009 | Brewer et al. | |
| 8,148,360 B2 | 4/2012 | Brewer et al. | |
| 8,445,475 B2 | 5/2013 | Brewer et al. | |

(Continued)

FOREIGN PATENT DOCUMENTS

DE    10214811 A1 * 10/2003    ............. A61N 5/062

OTHER PUBLICATIONS

Lilge et al. Evaluation of a Ruthenium coordination complex as photosensitizer for PDT of bladder cancer: cellular response, tissue selectivity and in vivo response. vol. 2, Issue1-2. Special Issue: Photodiagnosis and Photodynamic Therapy. Feb. 5, 2020. https://doi.org/10.1002/tbio.201900032 (Year: 2020).*

(Continued)

*Primary Examiner* — Shirley X Jian
(74) *Attorney, Agent, or Firm* — Caesar Rivise, PC

(57) ABSTRACT

An apparatus for irradiating inside an object is disclosed, including a lumen having a longitudinal axis; optical fibers within the lumen and aligned with the longitudinal axis; and an illumination member moveable or fixed within the lumen along the longitudinal axis. The apparatus can be used in a method for irradiating inside an object, including the steps of: providing an object having a cavity defined by an internal surface; inserting the lumen into the cavity; activating the illumination member to irradiate the internal surface with emitted light; receiving in each of the optical fibers light redirected from the internal surface; conveying the redirected light in a proximal direction through the plurality of optical fibers; and analyzing the redirected light conveyed through the plurality of optical fibers.

28 Claims, 12 Drawing Sheets

(56) References Cited

U.S. PATENT DOCUMENTS

| | | | |
|---|---|---|---|
| 9,345,769 B2 | 5/2016 | McFarland | |
| 9,737,565 B2 | 8/2017 | Mandel | |
| 11,241,587 B2* | 2/2022 | Lilge | A61B 5/0084 |
| 2001/0055462 A1* | 12/2001 | Seibel | A61B 1/00048 |
| | | | 385/33 |
| 2005/0075704 A1 | 4/2005 | Tu et al. | |
| 2006/0195165 A1 | 8/2006 | Gertner et al. | |
| 2008/0129993 A1 | 6/2008 | Brennan et al. | |
| 2016/0039854 A1 | 2/2016 | McFarland | |
| 2017/0100606 A1* | 4/2017 | Lilge | A61B 5/202 |

OTHER PUBLICATIONS

Thompson et al. Clinical system for interstitial photodynamic therapy with combined online dosimetry measurements. Applied Optics. vol. 44, No. 19. Jul. 2005. (Year: 2005).*

International Search Report for PCT/IB2016/056061 mailed Jan. 3, 2017.

Kassouf et al. Canadian guidelines for treatment of non-muscle invasive bladder cancer: a focus on intravesical therapy. Can Urol Assoc J. Jun. 2010;4(3):168-73. doi: 10.5489/cuaj.10051. PMID: 20514279; PMCID: PMC2874590.

Lazic et al., "Photodynamic therapy for Non-Muscle Invasive Bladder Cancer (NMIBC) mediated by instilled photosensitizer TLD1433 and green light activation", Photochemical & Photobiological Sciences 15, No. 4 (2016): 481-495.

Lilge et al. "Evaluation of a ruthenium coordination complex as photosensitizer for PDT of bladder cancer: cellular response, tissue selectivity and in vivo response." Translational Biophotonics (2020): e201900032.

Abstract of Van Staveren et al. "Integrating sphere effect in whole-bladder-wall photodynamic therapy: III. Fluence multiplication, optical penetration and light distribution with an eccentric source for human bladder optical properties." Physics in Medicine & Biology 41, No. 4 (1996).

* cited by examiner

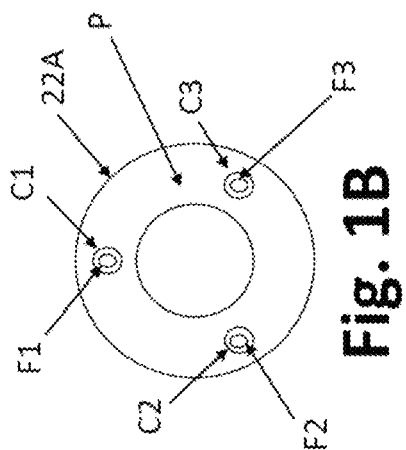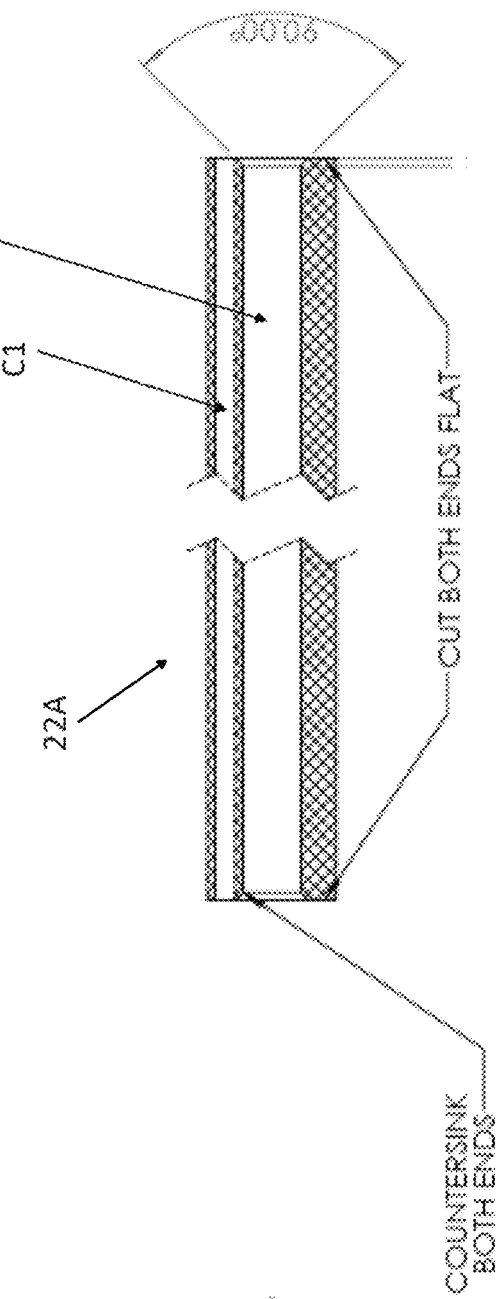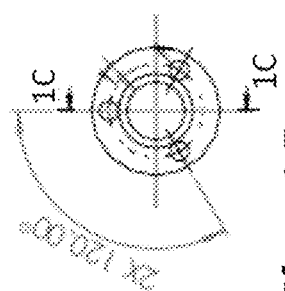

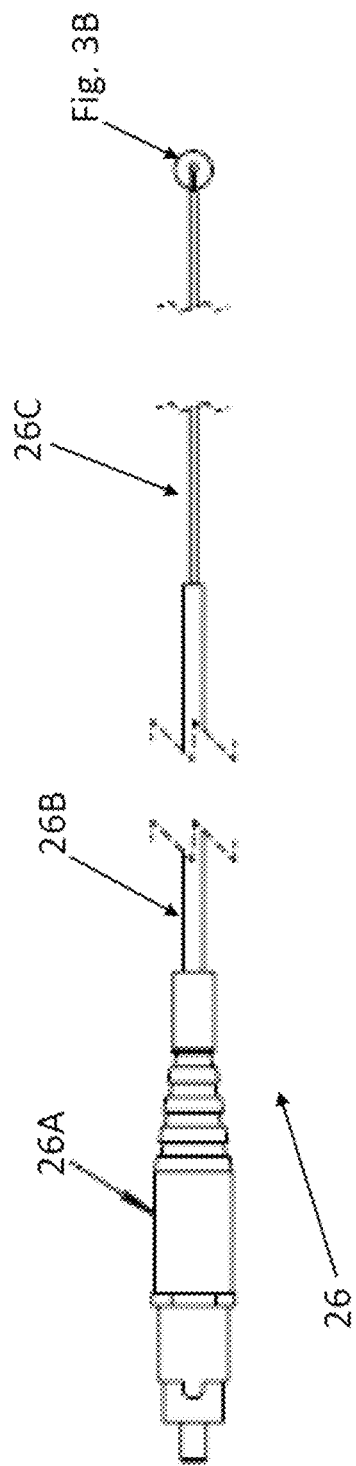
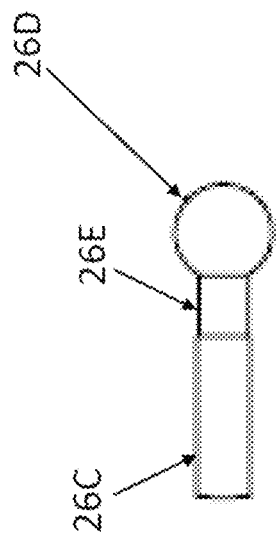
Fig. 3A
Fig. 3B

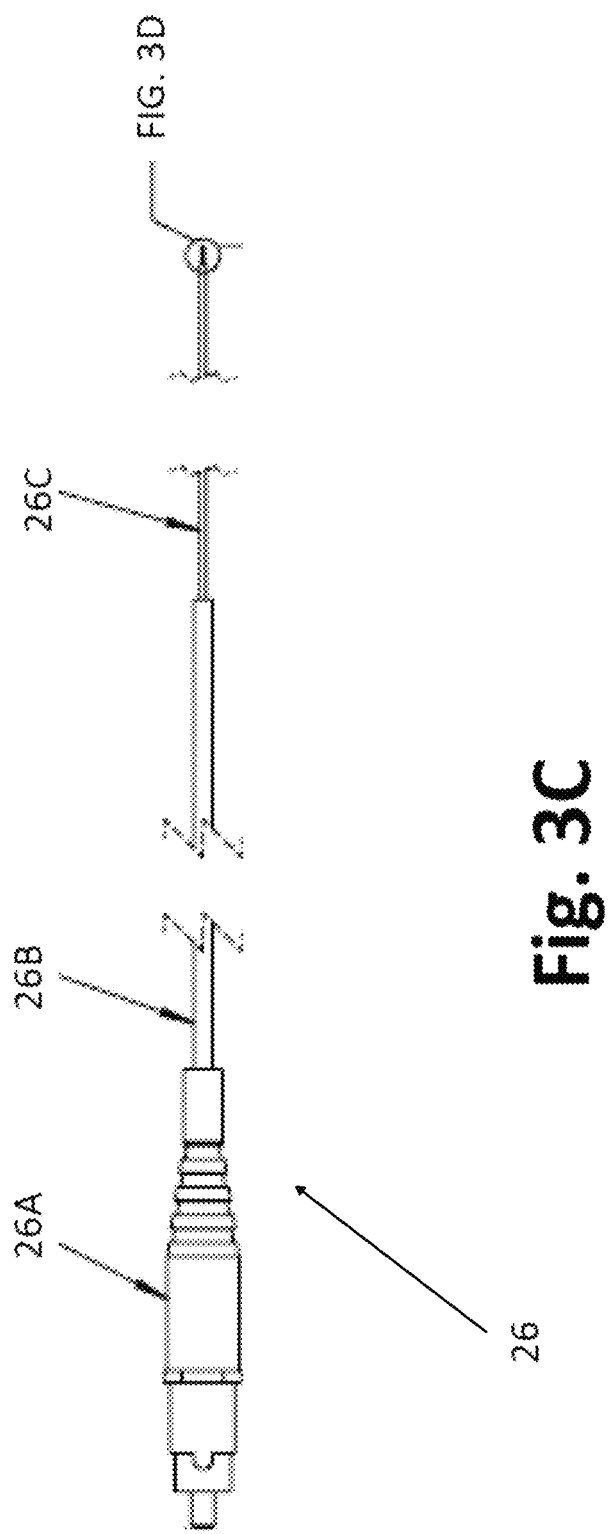

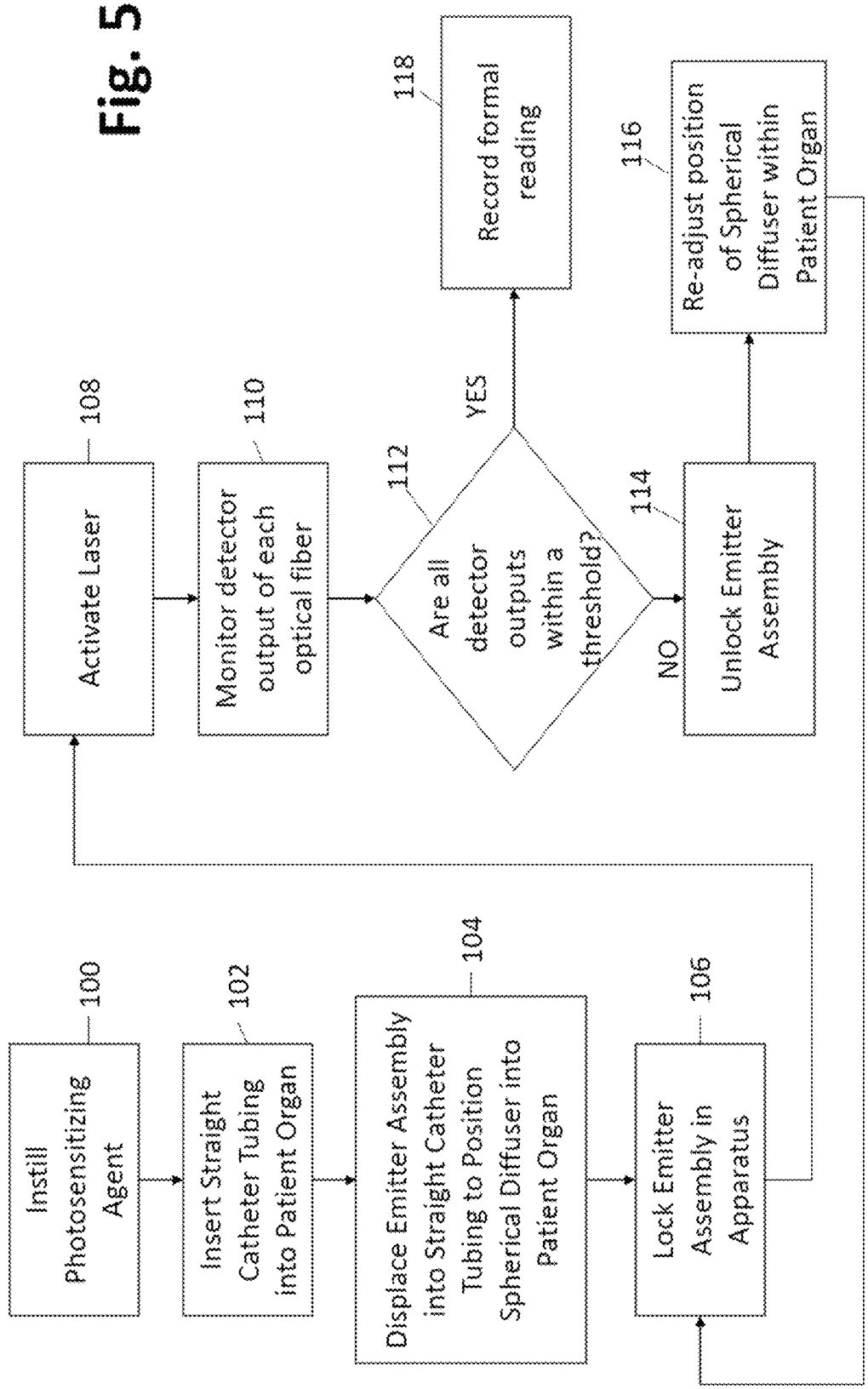

APPARATUS AND METHOD FOR IRRADIATING INSIDE AN OBJECT

FIELD OF THE INVENTION

The invention relates to the delivery and monitoring of light within an object. In particular, a method and apparatus are disclosed for providing light within a body cavity and/or hollow organ, such as a bladder or lung or other organ and for monitoring the irradiance ($W/cm^2$), treatment time (seconds) and/or energy density ($J/cm^2$) within that body cavity and/or hollow organ from at least one location, during single or multiple procedures.

BACKGROUND OF THE INVENTION

A variety of methods exist for applying light to treat diseases and undesirable conditions in humans and other animals, including (Low Level Laser Therapy ("LLLT") (also known as Cool Laser Therapy ("CLT")) and Photo Dynamic Therapy ("PDT").

LLLT or CLT generally requires the injured tissue to be exposed directly to laser light at a power density ($W/cm^2$) and treatment time (seconds) to deliver sufficient energy density ($J/cm^2$) at tissue depth to treat the condition; however, insufficient power density, treatment time and/or energy density to ablate or otherwise damage the target tissue. Exposure to laser light not only lessens the pain associated with certain disorders, but can significantly speed the healing of the treated tissues. See, e.g., U.S. Pat. No. 6,413,267 B1.

PDT involves the use of one or more photodynamic compounds ("PDCs") (also referred to as photosensitizers ("PSs")) and/or formulations thereof including other substances delivered to a patient by various means (e.g., topically, intravenously, via inhalation, intraperitoneally and/or intravesically), wherein the PSs are activated when exposed to light to induce oxidative stress/damage to a cell or tissue (i.e., intracellular damage or damage via vascular acting PSs). In particular, light is used to activate a PS to destroy tumors and tumor vasculature and to induce an immune response. Following photoactivation, the PS delivers a toxic burst of cytotoxic singlet oxygen and other Reactive Oxygen Species ("ROS") that are confined spatially and temporally to the irradiated region, thus targeting malignant tissue while sparing healthy tissue.

PDT is a promising technology for treating cancer, as well as for treatment of other diseases associated with unwanted and/or hyperproliferating cells such as non-malignant lesions.

Bladder cancer is among the cancers that have been treated with PDT. The American Cancer Society's estimates for bladder cancer in the United States for 2020 are approximately 81,400 new cases of bladder cancer (about 62,100 in men and 19,300 in women) and approximately 17,980 deaths from bladder cancer (about 13,050 in men and 4,930 in women). The Canadian Cancer Society estimates that 7,900 people in Canada will be diagnosed with bladder cancer this year, making it the fifth most common cancer in Canada (fourth most common among men, with 5,900 cases and twelfth most common among women with 2,000 cases).

With a recurrence rate of nearly 80%, bladder cancer is the most expensive cancer to treat on a per patient basis. The high recurrence rate raises many issues affecting quality of life because of its persistence.

The Canadian Urology Association Journal issued a guideline for the treatment of Non-Muscle Invasive Bladder Cancer ("NMIBC") in 2010. This guideline provides a Canadian consensus on the management of NMIBC. According to this guideline, the Transurethral Resection of Bladder Tumor ("TURBT") procedure is the first-line and gold standard treatment for NMIBC.

Intravesical therapy can be either chemotherapy or immunotherapy and is either therapeutic, prophylactic or adjuvant in the immediate postoperative setting.

Treatment options for recurrent bladder cancers are limited and often consist of systemic chemotherapy combined with or without a radical cystectomy. A radical cystectomy is the removal of the entire bladder, nearby lymph nodes, part of the urethra, and nearby organs that may contain cancer cells. In men, the prostate, the seminal vesicles, and part of the vas deferens are also removed. In women, the cervix, the uterus, the ovaries, the fallopian tubes and part of the vagina are also removed.

Intravesical therapy for patients with superficial papillary bladder cancer at risk for tumor recurrence appears reasonable, provided the therapy requires a limited number of treatments to be delivered, causes minimal toxicity to the patient and can delay recurrence for a reasonable length of time. Other active agents with a more favorable safety profile than Bacillus Calmette-Guérin ("BCG") need to be identified for prophylactic use in this patient population. Prevention of superficial recurrences is important as it would spare the patient further urinary symptoms and repeated TURBT procedures and the potential risk with associated complications and mortality, particularly in older patients, as well as to decrease the requirement for quarterly cystoscopic follow-up and the anxiety associated with discovery of new tumor growths.

U.S. Pat. No. 5,125,925 discloses a device said to be useful for treating bladder cancer, which comprises a fiber optic light source and single sensing optical fibers inserted into the bladder that senses light at its tip or along its length at any sensor and/or detector location.

US20170100606 A1 discloses a device that is particularly useful for treating bladder cancer with PDT. In this device, an illumination member is positioned within a collapsible cage formed of a plurality of optical fibers that contain light detectors therein. The illumination member and the optical fibers are controlled via communication with a computer. The cage is collapsible so that the entire illumination member and plurality of optical fiber assembly can be passed through a catheter inside a cystoscope and positioned within a body organ. When the assembly emerges from the distal of the catheter, the optical fibers of the cage expand inside the body organ and after the desired orientation within the body organ is achieved, PDT can proceed.

Despite the foregoing developments, there is still room in the art for improvement. In particular, it is desired to provide devices for conducting PDT and other light therapies within body cavities, which are of relatively simple and robust construction, and have uniform detector input. It is further desired to detect only diffuse reflectance from the bladder wall and to minimize direct light stimulation and potential saturation of the detectors by the emitter. It is further desired to provide such devices having improved ease of use.

All references cited herein are incorporated herein by reference in their entireties.

SUMMARY OF THE INVENTION

A first aspect of the invention comprises an apparatus for irradiating inside an object, said apparatus comprising: a lumen having a longitudinal axis; a plurality of optical fibers within the lumen and aligned with the longitudinal axis; and an illumination member that is moveable or fixed in location relative to the detectors within the lumen along the longitudinal axis, wherein: the object has a cavity defined by an internal surface; the apparatus is configured to activate the illumination member to irradiate the internal surface with emitted light; and each optical fiber of the plurality of optical fibers is a detector configured to receive redirected light from the internal surface and convey the redirected light in a proximal direction through the optical fiber for analysis, wherein any segments of the optical fibers extending distally beyond the distal end of the lumen remain aligned with the longitudinal axis of the lumen in use.

A second aspect of the invention comprises a method for irradiating inside an object, the method comprising the steps of: providing the inventive apparatus; providing the object having the cavity defined by the internal surface; inserting the lumen into the cavity; activating the illumination member to irradiate the internal surface with emitted light; receiving in each optical fiber of the plurality of optical fibers redirected light from the internal surface, wherein the receiving step is conducted with distal ends of the plurality of optical fibers within a circumference defined by the lumen; conveying the redirected light in a proximal direction through the plurality of optical fibers; and analyzing the redirected light conveyed through the plurality of optical fibers.

BRIEF DESCRIPTION OF THE DRAWINGS

FIG. 1B is a cross-sectional view of the straight lumen taken along line 1B-1B of FIG. 1A;

FIG. 1C is a cross-sectional view of the straight lumen taken along line 1C-1C of FIG. 1D;

FIG. 1D is a cross-sectional view of the straight lumen, similar to the view of FIG. 1B but with the optical fibers omitted and showing exemplary dimensions of the straight lumen;

FIG. 3A is a side view of the emitter assembly shown partially;

FIG. 3B is an enlarged view of the distal end of the emitter assembly showing the spherical diffuser;

FIG. 3C is side view of the emitter assembly, shown partially, and with the spherical diffuser omitted from the distal end and showing exemplary dimensions of portions of the emitter assembly;

FIG. 5 is a flowchart diagram illustrating a method in accordance with an exemplary embodiment of the invention;

DETAILED DESCRIPTION OF PREFERRED EMBODIMENTS

Apparatus

Figure 1A:
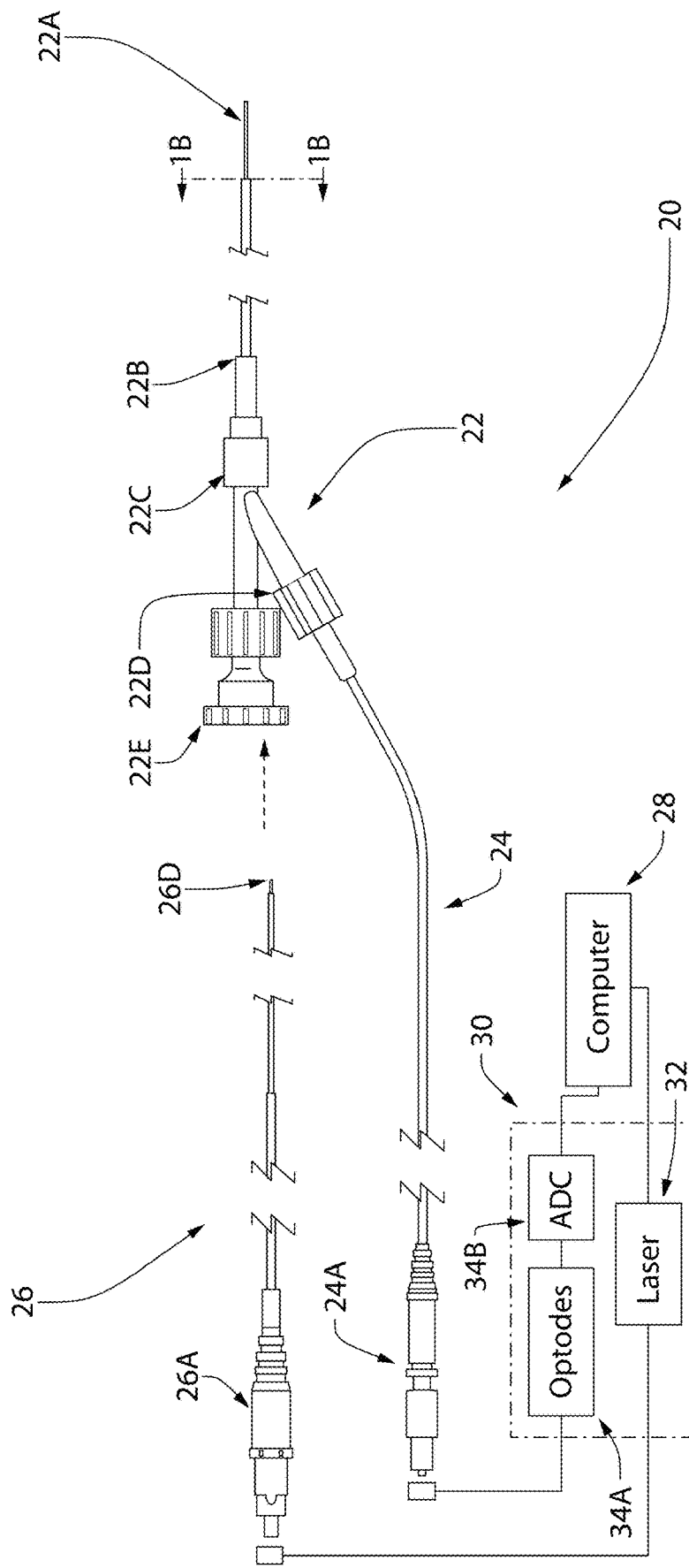
FIG. 1A depicts the spherical diffuser light delivery and fiber optic monitoring apparatus of the invention.

A first aspect of the invention comprises an apparatus for irradiating inside an object.

The apparatus comprises a lumen, a plurality of optical fibers and an illumination member.

The plurality of optical fibers (e.g., 2, 3, 4, 5 or more) is within the lumen and aligned with the longitudinal axis of the lumen. This means that at least a segment of each optical fiber is inside a longitudinal channel of the lumen and is therefore aligned with the longitudinal axis of the lumen. In addition, any segments of the optical fibers extending distally beyond the distal end of the lumen preferably remain aligned with the longitudinal axis of the lumen in use. Thus, the distal ends of the optical fibers are not bent away from the longitudinal axis of the lumen to form a bulbous cage, but rather run parallel to said axis. The optical fibers are preferably embedded within a side wall of the lumen. More preferably, the optical fibers are positioned within a sidewall of the lumen equidistantly around a circumference of the lumen.

The optical fibers are preferably silica core fibers. More preferably the optical fibers comprise a silica core of 25 to 100 μm and 50 to 250 μm of glass cladding, which have a Numerical Aperture ("NA"), preferably of 0.15 to 0.50.

In preferred embodiments, the proximal end of each optical fiber is coupled to a respective optode for measuring at least one of irradiance, treatment time and/or energy density associated with the redirected light received by the respective optode. The optodes convert the optical signal from a respective optical fiber into an electrical signal which is preferably digitized in a respective analog-to-digital converter for further processing. The optodes preferably comprise an optical sensor which optically measures the detected light and transforms the detected light into an electrical signal through an embedded preamplifier circuit. Suitable optodes; include, but are not limited to optodes able to detect light in the visible to near infrared range (300 to 1,500 nm) and optical powers (μW to Watts) range.

In preferred embodiments, the distal end of each detector and emitter optical fiber is cleaved or preferentially polished to provide each of the distal ends with a clean surface for detecting the redirected light and emitting light, respectively, through a predetermined light acceptance angle, while preventing direct reception of the emitted light and for mounting the spherical diffuser for homogenous light distribution, respectively. The predetermined light acceptance angle is preferably 15-180°, more preferably 15-90° and most preferably 15 to 45°.

The apparatus further comprises an illumination member that is moveable or fixed relative to the detectors within the lumen along the longitudinal axis of the lumen such that the illumination member can be deployed or fixed proximally, distally or in alignment to the distal end of the lumen and into the cavity. The illumination member's distal end is preferably a spherical diffuser, but could be a cylindrical or oblong diffuser or any other three dimensional shape suitable to illuminate the cavity in question.

In further embodiments, the plurality of optical fibers and spherical diffuser may be encapsulated inside a barrier material, which is reasonably optically clear or diffusive and prevents the penetration of bodily fluids and infectious agents, such as bacteria and viruses. The barrier material is preferably a resilient material, such as plastic, rubber, resin or other, which increases the robustness and ease of sterilization of the apparatus for clinical use.

The illumination member preferably comprises a spherical diffuser on a distal end thereof, which emits the emitted light omnidirectionally when the illumination member is activated. In certain embodiments, the spherical diffuser preferably has a diameter of 100-2000 μm or 500-1000 μm or 700-900 μm.

The proximal end of the illumination member is connected to a light source, which is preferably a laser. The laser is preferably emitting in the visible to near infrared range (300 to 1500 nm).

Suitable wavelengths for use in the invention range from 300 to 1500 nm.

In preferred embodiments, the apparatus further comprises a releasably locking adapter, which permits the illumination member to be releasably locked to maintain a position of the spherical diffuser at a desired distance beyond the distal end of the lumen or at a desired location within the cavity.

In preferred embodiments, the apparatus further comprises a controller, which is under the command of a computer. The computer processes and controls digitized signals from the controller's embedded optodes and light source.

The dimensions of the apparatus and the internal components thereof are largely dictated by the object to be irradiated. In a particularly preferred embodiment wherein the object to be irradiated is a bladder of an animal, the lumen and the components therein must be sized to fit through a urethra and have a length exceeding the length of the urethra. Suitable dimensions can be selected based on the species of animal to be treated. Due to the design of the urinary system, gender and age become relevant factors.

In embodiments wherein the object to be irradiated is an animal body part other than the bladder or an inanimate object, suitable dimensions of the lumen and components therein can likewise be selected based on the size, location and accessibility of the cavity in the object.

Referring to the figures, FIG. 1A illustrates an apparatus 20 in accordance with an exemplary embodiment of the invention. Apparatus 20 comprises a Y-connector 22 that receives a detector fiber assembly 24 and an emitter assembly 26 through respective portions of the Y-connector 22. A straight lumen 22A of the Y-connector 22 comprises a central passageway P (FIG. 1C) that permits passage of the spherical diffuser 26D therethrough. In addition, the walls of the straight lumen 22A also comprise three longitudinal and parallel channels C1-C3 (FIGS. 1B-1D) that house respective exemplary optical fibers F1-F3 (e.g., 50 μm core silica core optical fiber, 0.22 NA and 125 μm cladding) that originate in the detector fiber assembly 24. The proximal ends of the detector fiber assembly 24 and the emitter assembly 26 are coupled to a controller 30, which is controlled by computer 28. The controller 30 comprises respective optodes 34A, which convert the optical signal from a respective optical fiber F1-F3 into an electrical signal, which is then digitized in a respective Analog-to-Digital Converter ("ADC") 34B and then transmitted to the computer 28. In addition, the controller 30 also contains a laser 32, controlled by the computer 28, for illuminating the spherical diffuser 26D at the distal end of the emitter assembly 26. As such, when the distal end of the straight lumen 22A is inserted into a hollow object, such as a body organ, with the spherical diffuser 26D protruding therefrom (e.g., proximally, distally or in alignment to the distal end of the lumen) (see FIG. 4) and then activated to illuminate the previously-deposited photosensitizer in the walls of the body organ, the distal ends of the optical fibers F1-F3 are able to detect at least one of the irradiance, treatment time and/or energy density in the redirected light. Preferentially, the spherical diffuser 26D is fixed in location proximal to the distal end of the lumen and detectors F1-F3, in order to detect only redirected light.

It should be noted, as shown in FIGS. 1B and 1C, that the preferred location of the channels C1-C3 are equidistantly spaced (i.e., 120°) around the circumference of the straight lumen 22A. Furthermore, the distal end of each optical fiber F1-F3 is not necessarily coterminous with the distal end of the straight lumen 22A.

By way of example only, as shown in FIG. 1A, the Y-connector 22 comprises the straight lumen 22A which is connected to an adapter having a female Luer 22B. The adapter is connected to a Luer Y-connector 22C. One branch of the Y-connector 22C comprises another adapter 22E (e.g., Tuohy Borst 0-9FR) which receives passage of the distal end of the emitter assembly 26. The other branch of the Y-connector 22C comprises an adapter having a male Luer 22D in which is received the optical fibers F1-F3 from the detector fiber assembly 24.

It should be noted that adapter 22E comprises a lock. When the lock is actuated, the emitter assembly 26 is prevented in moving through the Luer Y-connector 22C. Thus, loosening the lock allows the emitter assembly 26 to move longitudinally through the Luer Y-connector 22C. In this manner, movement of the emitter assembly 26, and as such, the position of the spherical diffuser 26D, within the patient organ may be controlled proximal, distal or in alignment to the distal end of the lumen. Preferentially, the spherical diffuser 26D is fixed in location proximal to the distal end of the lumen and detectors F1-F3, in order to detect only redirected light.

Figures 2A, 2B:
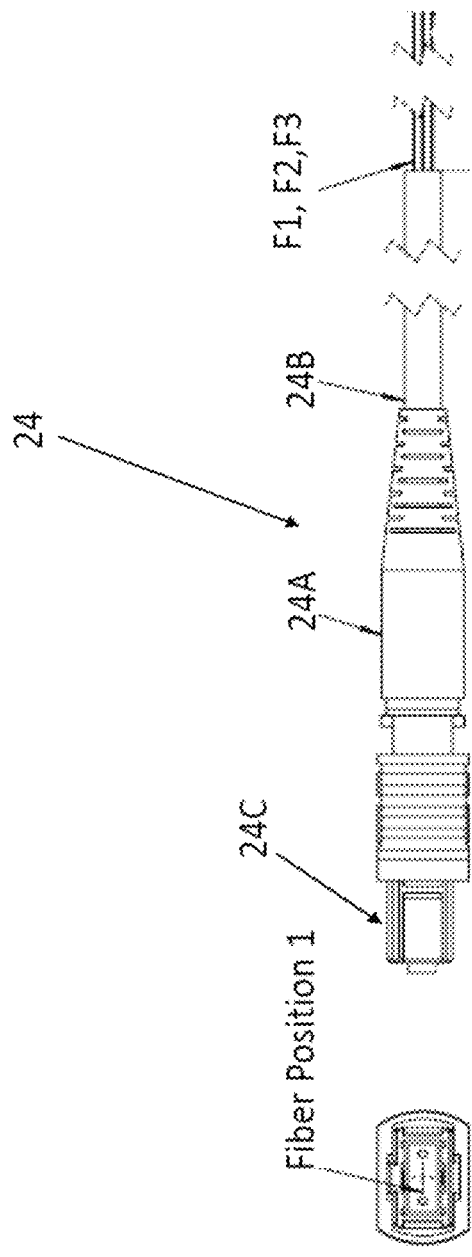
FIG. 2A is a side view of the detector fiber pigtail shown partially.
FIG. 2B is a plan view of the connector located on the proximal end of the detector fiber pigtail.
Figure 3D:
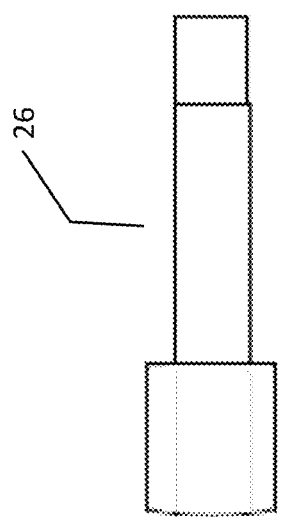
FIG. 3D is an enlarged view of the distal end of the emitter assembly with the spherical diffuser omitted.
Figure 3G:
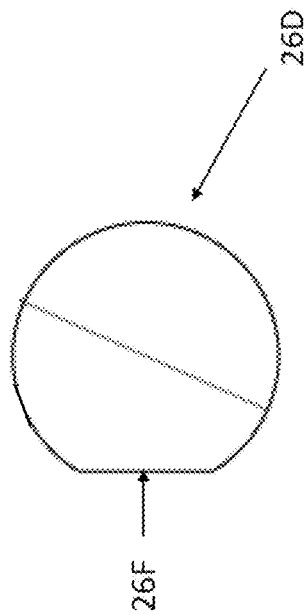
FIG. 3G is a side view of the spherical diffuser showing an exemplary diameter dimension thereof.
Figure 3F:
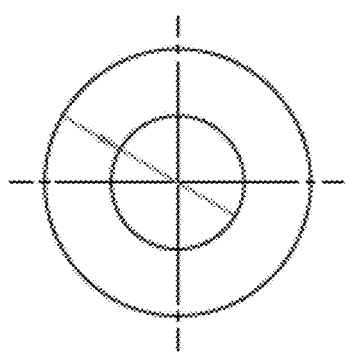
FIG. 3F is a plan view of the spherical diffuser showing exemplary dimensions of the central cavity for receiving the distal end of the emitter assembly therein.
Figure 3E:
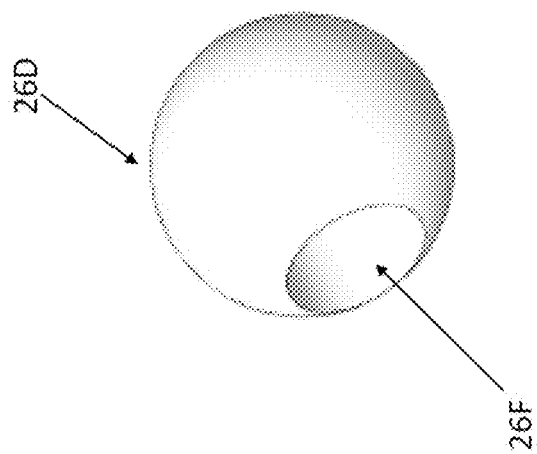
FIG. 3E is an isometric view of the spherical diffuser of the emitter assembly.

FIGS. 2A-2B depict an exemplary detector fiber assembly 24. The three (by way of example only) optical fibers F1-F3 emerge from a jacket 24B (e.g., 2 mm diameter), which in turn emerges from a connector 24A (e.g., MTP connector female). The proximal end of the connector 24A comprises an optical connector 24C (FIG. 2B) that connects to the optodes 34A in the controller 30.

The emitter assembly 26, depicted in FIGS. 3A-3G, comprises a connector 26A (e.g., SMA-905 Male-Metal Ferrule) on its proximal end. The ferrule at the proximal end of connector 26A couples to an optical fiber that connects the laser 32 in the controller 30 to the emitter assembly 26. On the distal side of connector 26A is a jacket 26B encasing an optical fiber 26C whose distal end 26E has the associated buffer and cladding removed (FIG. 3B) so as to fit within a cavity 26F (FIG. 3E) of the spherical diffuser 26D.

Figure 4:
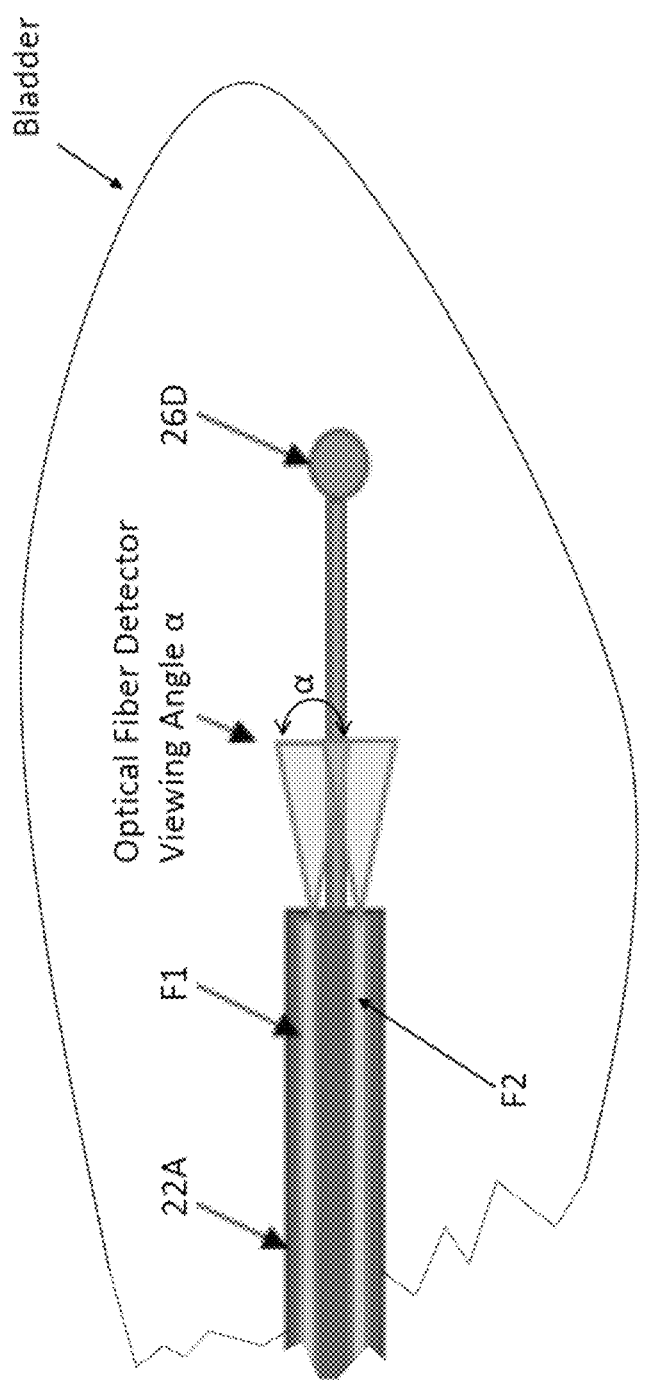
FIG. 4 is a functional diagram of the distal end of the emitter assembly depicting the detector view angle of two of the plurality of optical fibers.

As shown in FIG. 4, when the distal end of the apparatus 20 is inserted into the patient organ to be treated (e.g., bladder) and the spherical diffuser 26D energized to illuminate the walls of the organ previously treated with the PS, the distal end of the fibers F1-F3 each exhibit an acceptance angle α (also referred to as the "optical fiber detector viewing angle"). Because the distal end of each optical fiber F1-F3 is cleaved or preferentially polished, the distal end of the optical fiber F1-F3 (as mentioned previously, e.g., a 50 μm core silica core optical fiber) exhibits the angle α (e.g., 25° dependent on NA) as to which light redirected from organ walls and entering the optical fibers F1-F3 will be transmitted down each optical fiber length to the optodes 34A in the controller 30.

The preferred position of the spherical diffuser 26D is proximal to the distal end of the straight lumen 22A (hence the detector fibers are more distal than the spherical diffuser) to avoid laser light from directly influencing the detector optical fibers F1-F3. As such, only scattered or diffuse reflected (i.e., "redirected") laser light from the internal body organ (e.g., bladder) wall will be measured by the detector optical fibers F1-F3 through their acceptance angle α, thus eliminating "light noise" and/or light saturation from the spherical diffuser 26D and detecting only redirected light from the bladder wall, equating to the irradiance delivered to the bladder wall by the spherical diffuser 26D.

The spherical diffuser 26D may be moved proximal, distal or in alignment to the distal end of the lumen in order to vary the location of spherical diffuser 26D in relation to the detector optical fibers F1-F3, within a bladder to vary the redirected light detected versus the direct light received from the spherical diffuser. Preferentially, the spherical diffuser 26D is fixed in location proximal to the distal end of the lumen and detectors F1-F3, in order to detect only redirected light. Preferentially, the operator will place the spherical diffuser 26D into the geometric center of the cavity, in order to provide a homogenous distribution of light on the cavity wall.

Method

A second aspect of the invention is a method for irradiating the inside of an object using the apparatus of the invention.

The method is suitable for use with any object having a cavity therein or in which a cavity can be provided. Objects can be inanimate or animate. The object is preferably a body part of an animal and more preferably a hollow organ of an animal, such as a bladder. Preferred animals are mammals, such as humans.

Although the method is preferably a PDT method comprising the use of a PS, the invention is not limited thereto. In alternative embodiments, irradiation is conducted without the use of a PS (e.g., to administer LLLT in an animal or to produce a light-induced change in an inanimate object).

Suitable PSs can be identified through routine experimentation using the present disclosure as a guide. Preferred PSs are supramolecular metal complexes such as those disclosed in U.S. Pat. No. 9,345,769 B2, US2016039854 A1, U.S. Pat. No. 6,962,910 B2, U.S. Pat. No. 7,612,057 B2, U.S. Pat. No. 8,445,475 B2 and U.S. Pat. No. 8,148,360 B2. More preferred are complexes according to formulas (I) and (II) of U.S. Pat. No. 9,345,769 B2, in particular ruthenium and osmium complexes including TLD-1433 (Ru(4,4'-dimethyl-2,2'-bipyridine)$_2$Cl$_2$), TLDOSH2B ([Os(biq)$_2$(LL)], (biq=2, 2'-biquinoline and LL=1,10-phenanthroline), TLDOsH2IP ([Os(biq)$_2$(LL)] imidazo[4,5-f][1,10]phenanthroline) and TLDOsH$_2$dppn ([Os(biq)$_2$(LL)] benzo[i]dipyrido-[3,2-a:2', 3'-c]phenazine).

PSs are preferably administered in an excipient or carrier. For the purposes of the present invention the term "excipient" and "carrier" are used interchangeably and are defined herein as "ingredients which are used in the practice of formulating a safe and effective pharmaceutical composition." Suitable carriers are well known to those skilled in the art and can be prepared in accordance with acceptable pharmaceutical procedures, such as, for example, those described in Remington's Pharmaceutical Sciences, 17th edition, ed. Alfonoso R. Gennaro, Mack Publishing Company, Easton, Pennsylvania. (1985).

In certain embodiments, PDC-containing compositions further comprise a metal-binding glycoprotein (preferably transferrin) as a delivery vehicle for metal-based photodynamic compounds, so as to facilitate delivery of the photodynamic compounds into a biological target. Non-limiting examples of such compositions, which are suitable for use in the inventive method, are disclosed in U.S. Pat. No. 9,737, 565 B2.

The method of the invention is effective to reduce pain; promote healing; treat, prevent or eradicate diseases that involve unwanted and/or hyperproliferating cell etiology, including cancer; treat or prevent infectious diseases (e.g., viral and/or bacterial infections); disinfect surfaces; sterilize surfaces; and/or induce a chemical reaction within an object. In preferred embodiments, the method is effective to reduce the size and/or prevalence of malignant tumors.

Referring to the figures, FIG. 5 is a flowchart diagram which illustrates the operation of an exemplary therapeutic embodiment of the invention. Although the flowchart describes the use of the invention in a bladder using a preferred PS, this is by way of example only. At step 100, after the volume of the bladder has been calculated, the PS is instilled into the bladder cavity via the urethra. Instillation of the PS should be sufficient to allow uptake of the PS into the tissues of interest. The bladder is then voided, rinsed and refilled with sterile water. At step 102, the straight lumen 22A is inserted into the bladder. At step 104, the spherical diffuser of the emitter assembly 26D is located to the geometric center of the bladder. At step 106, the emitter and detector assembly is locked into place.

At step 108, irradiation commences to photoactivate the PS.

The target irradiance is preferably less than the Maximum Permissible Exposure ("MPE") according to IEC-60825: 2014 guidelines for tissue (visible wavelengths<200 mW/cm$^2$ and for NIR wavelengths<500 mW/cm$^2$), more preferably <150 mW/cm$^2$ for visible wavelengths and <400 mW/cm$^2$ for NIR wavelengths, to avoid tissue damage by PDT. Irradiation continues for a specified target treatment time to allow photoactivation of the PS; however, information that is made available in accordance with an exemplary embodiment of the invention is desirably considered when deciding at what target treatment time the irradiance is completed.

For set-up confirmation purposes, upon inserting the emitter and detector assembly into the bladder, operation of the laser light source 32 is commenced at a setup power (10% of target power density) and irradiance readings are obtained and displayed on a screen (not shown). At step 110, the detector optical fiber outputs are monitored. At step 112, the operator and/or computer software, in a further embodiment of the invention, determines if all the detector outputs are within a certain safety threshold. If they are not, the operator moves to step 114 to unlock the emitter and detector assembly and then onto step 116 to re-adjust the position of the emitter and detector assembly within the bladder, repeating steps 106 to 122 until all the detector optical fiber outputs indicate irradiance readings within a certain safety threshold, such as <MPE at the indicated wavelength. An audible and/or visual alarm may be sounded when the readings are outside the certain safety threshold.

Once all the detector optical fiber outputs are below the certain safety thresholds, at step 118, radiant exposure readings (J/cm$^2$) of the detector optical fiber outputs may be displayed on a screen. Operation of laser 32 is then commenced at a target power density. In one exemplary embodiment of the invention, irradiance (mW/cm$^2$) measurements are collected every second and the energy density (J/cm$^2$) is integrated over this time, providing the operator with a cumulative total and/or graphical representation of the cumulative energy density from the average of the detector optical fibers since the treatment commenced.

In a further exemplary embodiment of the invention, the ongoing irradiance can be monitored for safety purposes to detect if the irradiance exceeds MPE at any point in time and/or the energy density to determine when the target energy density detected by the average of the detector optical fibers F1-F3 will be attained.

After the calculated treatment time has elapsed, operation of laser 32 is discontinued and the emitter and detector assembly is removed from the bladder.

Figures 6A, 6B:
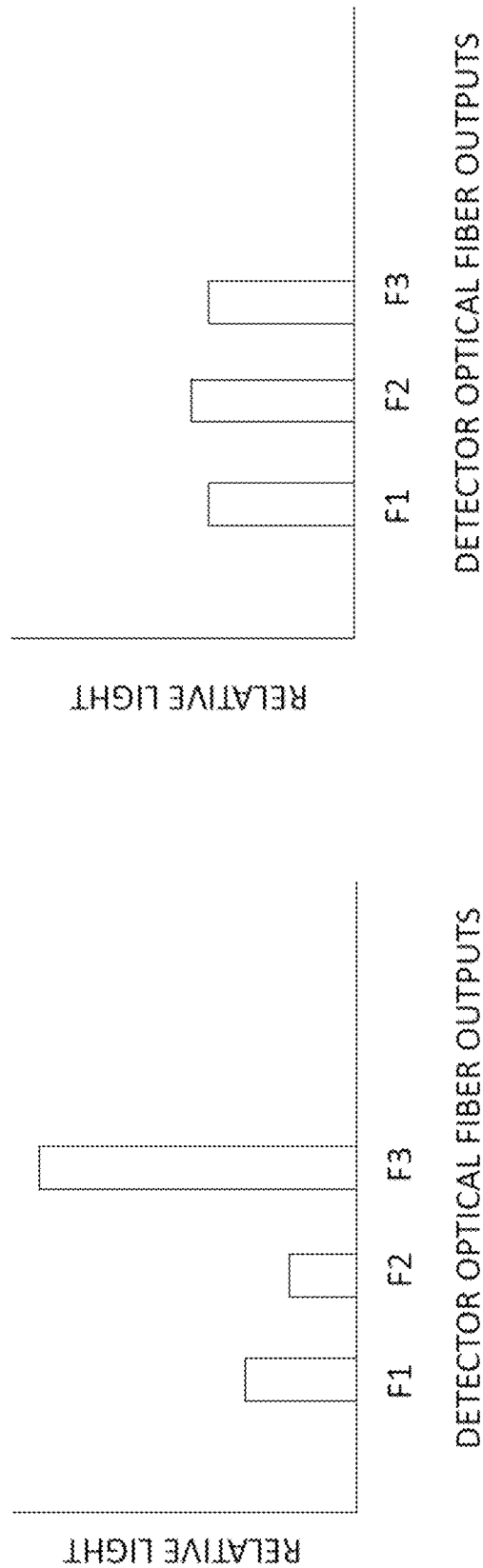
FIG. 6A and FIG. 6B are bar graphs that illustrate exemplary data obtained by performing data acquisition in accordance with an exemplary embodiment of the invention.

As previously explained, depending upon numerous factors such as the location of spherical diffuser 26D within the bladder, the size of the bladder, the shape of the bladder, the existence of cancer within the bladder, etc., the magnitude of light received by each of the detector optical fibers may vary. After the magnitude of light received by each of the detectors is stored in computer 28, computer 28 may generate a visual display which allows the operator to understand the relative amount of light being received by each of the detectors. FIG. 6A illustrates one such visual display. As shown in FIG. 6A, optical fiber F3 is receiving a higher magnitude of light than average, while optical fibers F1 and F2 are receiving a lower magnitude of light than average. After seeing the visual display that is exemplified in FIG. 6A, the operator may change the physical location of the spherical diffuser 26D within the bladder or relative to the detectors. After changing the location of spherical diffuser 26D within the bladder or relative to the detectors, the operator may then view a further visual display of the relative magnitude of light being received by all of the detector optical fibers F1-F3. A further exemplary visual display is illustrated in FIG. 6B. As shown in FIG. 6B, the average magnitude of light being received by detector optical fibers F1-F3 is substantially the same. In one exemplary embodiment of the invention, the magnitude of light received by each of the detector optical fibers F1-F3 may not be equivalent, but may be sufficiently close so that subsequent irradiation and activation of the PS may occur. In any event, once the operator sees from a visual display that the relative magnitude of light received by each of the optical fibers F1-F3 is sufficiently close or not sufficiently close in their direction, laser 32 may be energized to provide a sufficient amount of light for activation of the photodynamic drug and the light may remain at that level for a sufficient time period to activate the PS.

It should be noted that use of the detector optical fibers F1-F3 embedded within the straight lumen 22A provides several significant advantages over previous illumination devices used in the PDT process; wherein, light detectors are positioned around the illumination source. For example, since the detector optical fibers F1-F3 are fixed within the straight lumen 22A, there is no longer a requirement for a complex light detection structure to pass through a lumen and then reconfigure beyond the lumen with the body organ, while surrounding the illumination source. As such, the invention avoids the need for such a complex structure. Moreover, since the only moving part is the emitter and detector assembly within the cystoscope or the emitter relative to the detector within the cystoscope, the apparatus 20 of the invention requires fewer adjustments, fewer parts and is therefore more robust and less prone to failure. Even further, with the detector optical fibers F1-F3 fixed in the straight lumen 22A, preferentially distal to the emitter, the response of these detector optical fibers F1-F3 is more uniform. Consequently, the apparatus 20 is also easier to manufacture; thereby, reducing manufacturing complexity and hence costs.

Example—Treatment of Bladder Cancer

The stages of bladder cancer predominantly follow a progression from Carcinoma in Situ ("CIS"), through to Ta or T1, known as Non-Muscle Invasive Bladder Cancer ("NMIBC") through to T2 and T3, known as Muscle Invasive Bladder Cancer ("MIBC") and finally T4, in which the cancer has spread outside the bladder cavity and has metastasized external to the bladder. Bladder cancer, once metastasized, can become life threatening; therefore, it is important to limit the spread of the disease by treatments within the bladder cavity to destroy the NMIBC and/or MIBC before it has metastasized.

A bladder lesion (or tumor) may be located on the wall of the bladder. In PDT, the primary objective is to induce a PS to be absorbed by bladder tumor cells. To accomplish this objective, a catheter is inserted through the patient's urethra and a certain volume and drug dose of a PS is instilled into the bladder. The larger the bladder, the greater the amount of volume and drug dose that is instilled into the bladder. Furthermore, the larger the size of the bladder, the greater the surface area of the bladder; thus, it is preferable to have a homogeneous distribution of the drug throughout the bladder. In an exemplary embodiment of the invention, the invention may be used in combination with a PS such as TLD-1433. In further embodiments of the device, the device may be used with or without a PS and is used to deliver light to the target, such as inflamed bladder tissues delivered with CLT or LLLT, in the treatment of inflammation, infection, irritation and/or pain.

After the PS has been instilled into the bladder, the PS is activated by a light source. It is preferable to have a homogeneous distribution of light within the bladder to uniformly activate the PS. Theoretically, it would be desirable to drain the PS from the bladder, fill the bladder with sterile water, insert a light emitter with spherical diffuser into the bladder and activate the light source. While theoretically such a procedure is desirable, in actuality, such a procedure may not work safely or effectively because the bladder varies significantly in physical characteristics between patients and is not a perfect sphere. Bladders come in many shapes, and sizes, with unique geometrical features all to themselves, lending to numerous anatomical and physical characteristics. Therefore, the amount of light that is deposited onto a bladder wall surface from a light emitter may vary significantly. There may be hot spots (excessive irradiation) and cold spots (insufficient irradiation) leading to variations in the activation of the PS and hence ability of the PS to destroy cancer cells. As a result, over-activation of a PS in some areas is possible, while in other areas, under-activation of the PS may occur. In further areas, the PS may not be activated at all.

A spherical diffuser having an outer diameter preferably of <2 mm and more preferably <1,000 μm is placed 1 to 20 mm proximal to the distal end of a lumen comprising three optical fibers, each containing light detectors (F1-F3). The optical detector fibers are positioned distal to the spherical diffuser to maximize the input of reflected light and to minimize direct detection of light emitted from the spherical diffuser. Therefore, preferably only redirected (i.e., scattered or reflected) laser light from the bladder wall is measured by the detector fibers through their acceptance angle, thus eliminating "light noise" from the spherical diffuser. As shown most clearly in FIG. 4, because the spherical diffuser 26D and the plurality of optical fibers F1-F3 are aligned along the longitudinal axis of the lumen 26, the inventive apparatus 20 is generally referred to as a "straight design" to distinguish it from the "cage design" of US 20170100606 A1, which uses a light source that is surrounded by "a cage" formed of a plurality of optical fibers having detectors therein.

Figure 7A:
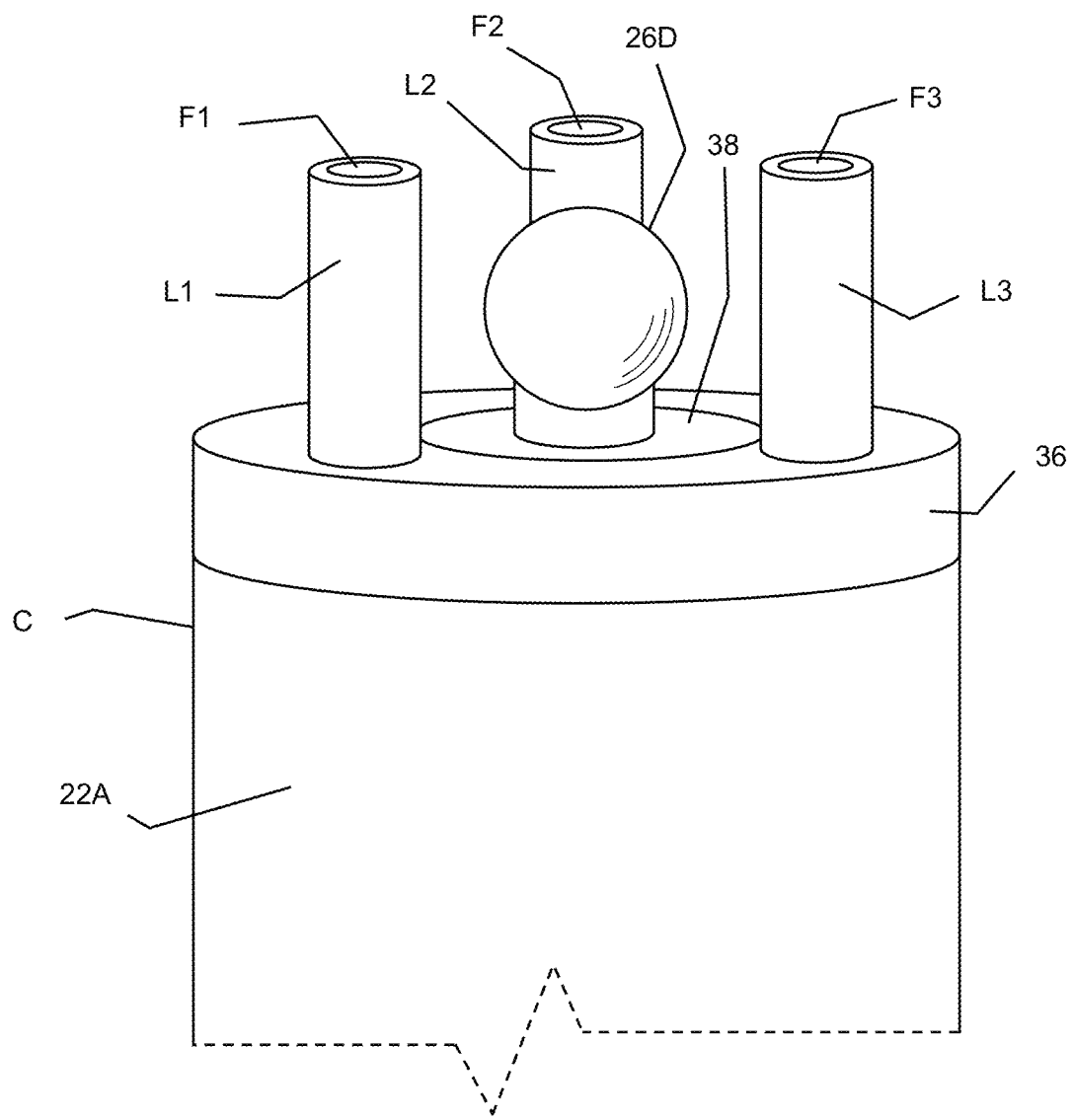
FIG. 7A is a side perspective view of an embodiment of a spacer mounted on a distal end of a lumen.
Figure 7B:
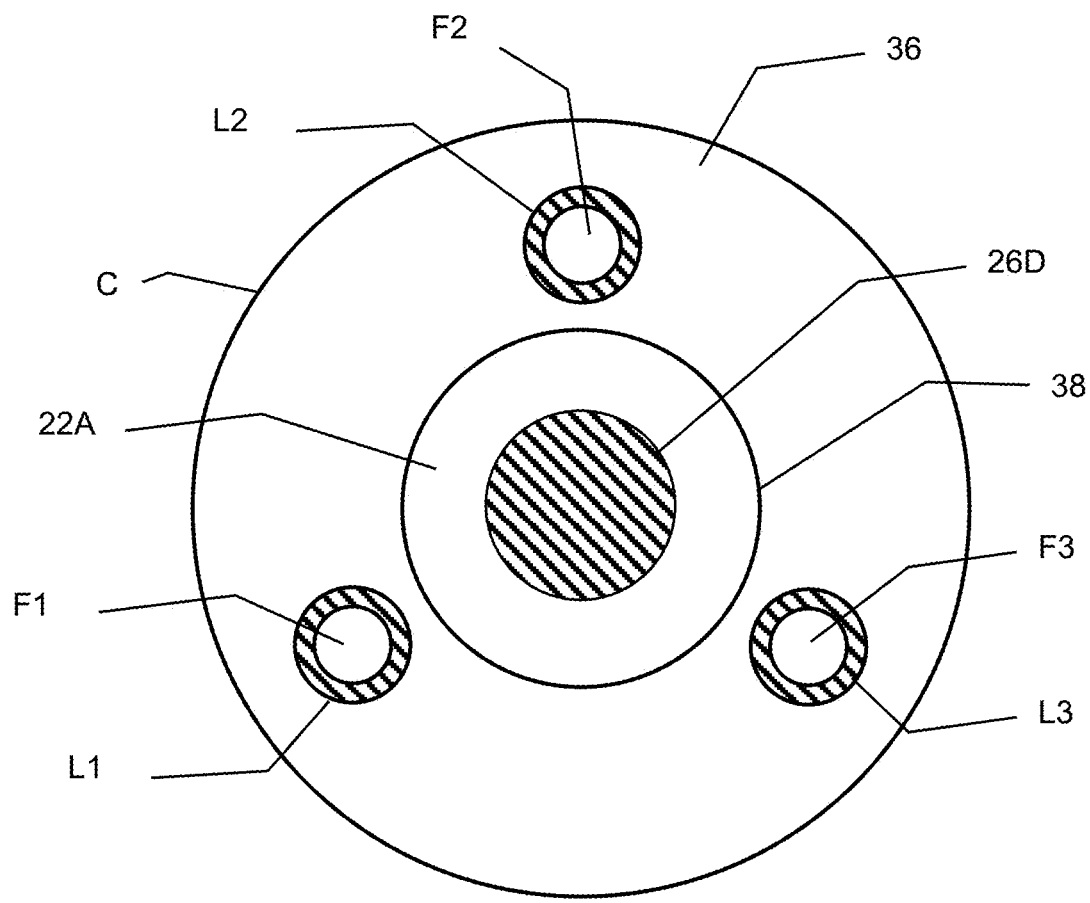
FIG. 7B is a distal end view of the spacer of FIG. 7A.

FIGS. 7A and 7B show an embodiment of the inventive apparatus wherein spacer 36 is mounted on the distal end of lumen 22A and distal segments of optical fibers F1, F2, F3 are respectively housed within legs L1, L2, L3 of spacer 36. The cleaved and preferably polished distal ends of the fibers F1, F2, F3 are flush with the distal ends of legs L1, L2, L3. Spherical diffuser 26D passes through center orifice 38 of spacer 36, or is fixed in location, such that it is maintained within a portion of the space defined by the legs L1, L2, L3. Spacer 36 thus prevents spherical diffuser 26D from contacting the cavity in which it is deployed. In addition, spacer 36 maintains the segments of optical fibers F1, F2, F3 extending distally beyond the distal end of lumen 22A within circumference C defined by the lumen 22A (which is the same as the circumference of spacer 36 in the embodiment of FIGS. 7A and 7B), unlike the cage design of US 20170100606 A1 wherein the optical fibers do not remain aligned with the longitudinal axis of the lumen but rather are expanded beyond the circumference of the lumen to form a bulbous cage. Spacer 36 is preferably attached to lumen 22A via at least one projection (or barb; not shown) from spacer 36 that is received by at least one corresponding hole (not shown) in lumen 22A. It is particularly preferable to use three barbs around the periphery of the spacer which fit within three corresponding holes around the periphery of the lumen, which are separated by 120 degrees each.

In further embodiments, the spacer, plurality of optical fibers and spherical diffuser may be encapsulated inside plastic, rubber, resin or other reasonably optically clear or diffusive resilient materials to increase robustness and ease of sterilization for clinical use.

The combination of the spherical diffuser and plurality of detector optical fibers is typically inserted through the working channel of a cystoscope of very small size (e.g., typically 4.5 mm (13.5 French) in diameter, in the case of a rigid cystoscope and typically 2.2 mm (6.6 French) in diameter for a flexible cystoscope). The spherical diffuser and plurality of detector optical fibers is typically inserted through the working channel of the cystoscope, which has been inserted through the urethra of a patient.

The detectors described herein are for measuring irradiance. It is understood that this is merely exemplary as other measurements, such as treatment time and energy density, may be included.

Because light is illuminating in a confined location, the bladder may act like an integrating sphere. Thus, light may be absorbed or may be redirected off the surface of the bladder and become incident onto another location of the bladder wall, from which it will be redirected again. The amount of redirected light varies according to the albedo (degree of "whiteness" or reflection coefficient), which may significantly affect the amount of light within a bladder at any particular location. This effect is known as the Multiplication Factor ("M Factor") for integrating spheres and has been demonstrated to be between 2 and 6 for the diseased human bladder. See, e.g., van Staveren et al. "Integrating sphere effect in whole-bladder-wall photodynamic therapy: III. Fluence multiplication, optical penetration and light distribution with an eccentric source for human bladder optical properties." Physics in Medicine & Biology 41, no. 4 (1996): 579.

If there is bladder cancer present, then there will be diseased tissue and as a result bladder lesions will typically absorb more light than healthy bladder tissue at some of the potential treatment wavelengths, providing variations in the amount of light absorbed by any particular bladder wall surface area.

The spherical diffuser and the plurality of detector optical fibers are deployed in a bladder to measure light exposure at a plurality of locations within the bladder. It is thus desirable to know the internal volume of the organ. It is desirable to know how much PS is to be instilled into the organ. A solution such as distilled water can be used to fill the organ until backpressure suggests to the operator that the bladder folds are effaced or bladder unfolding has been verified by the viewing optics of the cystoscope. In the case of a bladder, exemplary bladder volumes, radii, surface areas, recommended power and treatment times are shown in Table 1 below.

TABLE 1

| Volume (ml) | Radius (cm) | Surface Area (cm$^2$) | Power (W) | Time (minutes) |
|---|---|---|---|---|
| 50 | 2.3 | 65.6 | 1.65 | 60 |
| 75 | 2.6 | 86.0 | 2.15 | 60 |
| 100 | 2.9 | 104.2 | 2.60 | 60 |
| 125 | 3.1 | 120.9 | 3.00 | 60 |
| 150 | 3.3 | 136.5 | 3.40 | 60 |
| 175 | 3.5 | 151.3 | 3.80 | 60 |
| 200 | 3.6 | 165.4 | 4.00 | 62 |
| 225 | 3.8 | 178.9 | 4.00 | 67 |
| 250 | 3.9 | 191.9 | 4.00 | 72 |
| 275 | 4.0 | 204.5 | 4.00 | 77 |
| 300 | 4.2 | 216.7 | 4.00 | 81 |
| 325 | 4.3 | 228.6 | 4.00 | 86 |
| 350 | 4.4 | 240.2 | 4.00 | 90 |
| 375 | 4.5 | 251.5 | 4.00 | 94 |
| 400 | 4.6 | 262.6 | 4.00 | 98 |
| 425 | 4.7 | 273.4 | 4.00 | 103 |
| 450 | 4.8 | 284.0 | 4.00 | 107 |
| 475 | 4.8 | 294.4 | 4.00 | 110 |
| 500 | 4.9 | 304.7 | 4.00 | 114 |
| 525 | 5.0 | 314.8 | 4.00 | 118 |
| 550 | 5.1 | 324.7 | 4.00 | 122 |
| 575 | 5.2 | 334.4 | 4.00 | 125 |
| 600 | 5.2 | 344.1 | 4.00 | 129 |
| 625 | 5.3 | 353.6 | 4.00 | 133 |
| 650 | 5.4 | 362.9 | 4.00 | 136 |
| 675 | 5.4 | 372.2 | 4.00 | 140 |
| 700 | 5.5 | 381.3 | 4.00 | 143 |
| 725 | 5.6 | 390.3 | 4.00 | 146 |
| 750 | 5.6 | 399.3 | 4.00 | 150 |
| 775 | 5.7 | 408.1 | 4.00 | 153 |
| 800 | 5.8 | 416.8 | 4.00 | 156 |
| 825 | 5.8 | 425.4 | 4.00 | 160 |
| 850 | 5.9 | 434.0 | 4.00 | 163 |
| 875 | 5.9 | 442.5 | 4.00 | 166 |
| 900 | 6.0 | 450.9 | 4.00 | 169 |
| 925 | 6.0 | 459.2 | 4.00 | 172 |
| 950 | 6.1 | 467.4 | 4.00 | 175 |
| 975 | 6.2 | 475.6 | 4.00 | 178 |
| 1000 | 6.2 | 483.7 | 4.00 | 181 |

The spherical diffuser delivers a target irradiance, treatment time and hence energy density to the target tissue. Said target irradiance includes the primary irradiance delivered by the isotropic emitter (spherical diffuser) and the diffuse reflectance from all bladder segments. The latter contribute to the M Factor of the bladder which acts as an integrating sphere. M Factors for the diseased bladder have been reported to range from 2 to 6, with the lower M factor typically associated to a low albedo (e.g., bladder with extensive disease) and little to none "normally white appearing" bladder wall; whereas, higher M Factors are typically associated with a high albedo (e.g., bladder with less extensive disease) and higher quantities of "normally white appearing" bladder wall.

Prior to use, the treatment power settings for the spherical diffuser and optical detector settings for the plurality of optical detectors are verified. In one exemplary embodiment of the invention, a "dongle" which connects the output of the laser engine and the input of the optical detectors is connected to the controller and energized with laser light to verify that the laser engine is emitting laser output and the optical detectors are receiving laser input within specified ranges.

The PS (TLD-1433) is typically supplied in a translucent or opaque glass vial, which has typically been sealed by inert gas and further sealed inside a light proof packaging, more preferably supplied in a Class III amber borosilicate glass vial, nitrogen gas sealed and heat sealed inside a foil lined plastic bag. The PS is subsequently reconstituted. The PS is reconstituted with sterile water in relation to the patient's bladder volume and surface area to preferentially achieve a clinical dilution of 0.70 mg/cm$^2$ for this particular PS and for other PSs. Other clinical dilutions may be equally beneficial. The final solution may be instilled in the bladder cavity (dwell time) preferentially for sixty minutes, but for this particular PS and for other PSs, other dwell times may be equally beneficial. The bladder is voided and a cystoscope is placed through the urethra to the bladder neck. Any surface bound PS is removed by flushing the bladder with sterile water. The bladder is desirably distended during treatment to efface the bladder wall to minimize folds in the bladder wall that may prevent uniform light illumination, as evidenced by the viewing optics of the cystoscope.

The distal end of the invention is then introduced into the bladder through the cystoscope and treatment is conducted as described above.

If the spherical diffuser moves during the above procedure and touches the bladder wall for any length of time, it is possible that the light emitter may cause thermal damage to the bladder wall, due to the high emission powers used to activate the PS. Such thermal damage may affect safety and tolerability of the procedure.

The cage design of US20170100606 A1 helps prevent the spherical diffuser from touching the bladder wall and has achieved positive results. See, e.g., Lazic et al. "Photodynamic therapy for Non-Muscle Invasive Bladder Cancer ("NMIBC") mediated by instilled photosensitizer TLD-1433 and green light activation." Photochemical & Photobiological Sciences 15, no. 4 (2016): 481-495; and Lilge et al. "Evaluation of a ruthenium coordination complex as photosensitizer for PDT of bladder cancer: cellular response, tissue selectivity and in vivo response." Translational Biophotonics (2020): e201900032.

The instant invention is based in part on the surprising discovery that a straight (cage-free) design provides many of the benefits of the cage design with less complexity in manufacturing, higher safety detection margins and use. Both the straight and cage designs can detect when the emitter approaches the wall of a cavity in which they are placed, with the added advantage that the straight design has a greater safety detection margin and can physically prevent the spherical diffuser from contacting the bladder wall by allowing the distal end of the detector to extend past the spherical diffuser a predetermined length. In the straight design disclosed herein, thermal damage to the wall can also be avoided by detecting a change in irradiance detected by the optical detectors, as the emitter is advanced towards the bladder wall and locking it into a position when such detection does not indicate contact or near contact with the bladder wall. In certain embodiments, the apparatus can further comprise at least one thermal sensor to detect temperature within the cavity and to provide safety information based on detection.

While the invention has been described in detail and with reference to specific examples thereof, it will be apparent to one skilled in the art that various changes and modifications can be made therein without departing from the spirit and scope thereof.

What is claimed is:

1. An apparatus for irradiating inside an object, said apparatus comprising:
   a lumen having a longitudinal axis;
   a plurality of optical fibers embedded and immovable within a sidewall of the lumen and aligned with the longitudinal axis; and
   an illumination member that is moveable or fixed within the lumen along the longitudinal axis,
   wherein:
   the object has a cavity defined by an internal surface;
   the apparatus is configured to activate the illumination member to irradiate the internal surface with emitted light; and
   each optical fiber of the plurality of optical fibers is a detector configured to receive redirected light from the internal surface and convey the redirected light in a proximal direction through the optical fiber for analysis, wherein any segments of the optical fibers extend distally beyond said illumination member, remain aligned with the longitudinal axis of the lumen in use, said detectors detecting only redirected light.

2. The apparatus of claim 1, wherein the optical fibers are fixed within said sidewall of the lumen equidistantly around a circumference of the lumen.

3. The apparatus of claim 2, wherein the illumination member comprises a spherical diffuser on a distal end thereof, the spherical diffuser emitting the emitted light omnidirectionally when the illumination member is activated.

4. The apparatus of claim 3, wherein the illumination member comprises a proximal end connected to a light source.

5. The apparatus of claim 4, wherein the light source comprises a laser.

6. The apparatus of claim 5, further comprising a spacer attached to the distal end of the lumen, wherein a distal segment of each of the optical fibers is housed within a respective leg of the spacer, a distal end of each of the optical fibers is flush with a distal end of the respective leg in which it is housed, and the spherical diffuser occupies a portion of a space defined by legs of the spacer such that the spacer prevents the spherical diffuser from contacting the cavity in which the spherical diffuser is deployed and maintains the optical fibers within a circumference defined by the lumen.

7. The apparatus of claim 1, wherein each one of the plurality of optical fibers comprises a proximal end, and wherein each proximal end is coupled to a respective optode for measuring at least one of irradiance, treatment time and energy density associated with the redirected light received by the respective optode.

8. The apparatus of claim 7, wherein each one of the plurality of optical fibers comprises a distal end that is cleaved or polished to provide each of the distal ends with a predetermined light acceptance angle effective to receive the redirected light while preventing direct reception of the emitted light, when said illumination member is proximal to the distal end of the plurality of optical fibers.

9. The apparatus of claim 8, wherein the plurality of optical fibers and the illumination member are encapsulated inside a barrier material that is optically clear and resistant to penetration by infectious agents and bodily fluids.

10. The apparatus of claim 8, wherein the predetermined light acceptance angle is 15 to 180°.

11. The apparatus of claim 1, further comprising a releasably locking adapter, the releasably locking adapter permitting the illumination member to be releasably locked to maintain a position of the illumination member at a desired location in the cavity or fixed in location relative to each optical fiber detector.

12. A method for irradiating inside an object, the method comprising the steps of:
providing the apparatus of claim 1;
providing the object having the cavity defined by the internal surface;
inserting the lumen into the cavity;
activating the illumination member to irradiate the internal surface with emitted light;
receiving in each optical fiber of the plurality of optical fibers redirected light from the internal surface, preventing direct reception of the emitted light, when the illumination member is proximal the distal end of the plurality of optical fibers, wherein the receiving step is conducted with distal ends of the plurality of optical fibers within a circumference defined by the lumen;
conveying the redirected light in a proximal direction through the plurality of optical fibers; and
analyzing the redirected light conveyed through the plurality of optical fibers.

13. The method of claim 12, wherein the optical fibers are fixed within said sidewall of the lumen equidistantly around the circumference of the lumen.

14. The method of claim 13, wherein the illumination member comprises a spherical diffuser on a distal end thereof, and the spherical diffuser emits the emitted light omnidirectionally when the illumination member is activated.

15. The method of claim 14, wherein a proximal end of the illumination member is connected to a light source.

16. The method of claim 15, wherein the light source is a laser.

17. The method of claim 16, wherein the apparatus further comprises a spacer attached to the distal end of the lumen, wherein a distal segment of each of the optical fibers is housed within a respective leg of the spacer, a distal end of each of the optical fibers is cleaved or polished and is flush with a distal end of the respective leg in which it is housed, and the spherical diffuser occupies a space defined by legs of the spacer such that the spacer prevents the spherical diffuser from contacting the cavity in which the spherical diffuser is deployed and maintains the optical fibers within the circumference defined by the lumen.

18. The method of claim 17, wherein the plurality of optical fibers and the spherical diffuser are encapsulated inside a barrier material that is optically clear and resistant to penetration by infectious agents and bodily fluids.

19. The method of claim 12, wherein each one of the plurality of optical fibers comprises a proximal end, each proximal end is coupled to a respective optode and the analyzing step comprises measuring at least one of irradiance, treatment time and energy density associated with the redirected light received by the respective optode.

20. The method of claim 12, wherein each one of the plurality of optical fibers comprises a distal end that is cleaved or polished to provide each of the distal ends with an ability to accept light at a predetermined acceptance angle and wherein the optical fibers are placed distal to the spherical diffuser, so that a majority of light received by the plurality of optical fibers is redirected light and a minority of emitted light is directly received by the plurality of optical fibers.

21. The method of claim 20, wherein the predetermined light acceptance angle is 15 to 180°.

22. The method of claim 12, wherein the lumen comprises a releasably locking adapter, and the method further comprises the step of releasably locking the illumination member to maintain a position of the illumination member at a desired location in the cavity or fixed in location relative to the detectors.

23. The method of claim 12, wherein the object is an organ within an animal and the method further comprises the step of administering a photosensitizing agent to the animal before the activating step.

24. The method of claim 23, wherein the animal is a human and the object is a bladder.

25. The method of claim 24, wherein the photosensitizing agent is a supramolecular metal complex of ruthenium or osmium.

26. The method of claim 25, wherein the method treats a cancerous tumor.

27. The method of claim 26, wherein the photosensitizing agent is TLD-1433.

28. The method of claim 12, wherein the object is an organ within an animal and the method treats at least one of inflammation, infection, irritation and pain.

* * * * *